United States Patent
Sundstrom et al.

(10) Patent No.: US 8,679,048 B2
(45) Date of Patent: Mar. 25, 2014

(54) OPTIMIZATION OF HYDROCEPHALUS SHUNT SETTINGS

(75) Inventors: Nina Sundstrom, Umea (SE); Anders Eklund, Umea (SE); Jan Malm, Umea (SE)

(73) Assignee: Likvor AB, Umea (SE)

( * ) Notice: Subject to any disclaimer, the term of this patent is extended or adjusted under 35 U.S.C. 154(b) by 846 days.

(21) Appl. No.: 12/798,227

(22) Filed: Mar. 30, 2010

(65) Prior Publication Data
US 2010/0262064 A1    Oct. 14, 2010

Related U.S. Application Data

(60) Provisional application No. 61/211,546, filed on Mar. 31, 2009.

(51) Int. Cl.
   *A61M 5/00*    (2006.01)

(52) U.S. Cl.
   USPC ............... 604/9; 604/317; 604/318; 604/322; 604/323; 604/327; 604/8; 604/10; 239/222; 239/238; 239/436

(58) Field of Classification Search
   USPC .................................... 604/8, 9, 10
   See application file for complete search history.

(56) References Cited

U.S. PATENT DOCUMENTS

| | | | |
|---|---|---|---|
| 7,104,958 B2 * | 9/2006 | Crutchfield et al. | 600/454 |
| 7,485,105 B2 * | 2/2009 | Wolf | 604/9 |
| 2002/0052563 A1 | 5/2002 | Penn et al. | |
| 2005/0187509 A1 | 8/2005 | Wolf | |
| 2006/0020239 A1 | 1/2006 | Geiger et al. | |

FOREIGN PATENT DOCUMENTS

| | | |
|---|---|---|
| DE | 19654990 A1 | 6/1998 |
| EP | 1749549 A1 | 2/2005 |
| EP | 1676527 A1 | 5/2006 |
| EP | 2008683 A1 | 12/2008 |
| JP | 11299742 | 2/1999 |
| JP | 3052238 B2 | 6/2000 |
| WO | WO 2006/091164 * | 8/2006 |
| WO | WO 2006/091164 A1 | 8/2006 |
| WO | WO 2006/091581 A1 | 8/2006 |

OTHER PUBLICATIONS

Miyake, H. et al., Development of a Quick Reference Table for Setting Programmable Pressure Valves . . . Neurol.Med.Chir.(Tokyo) 48:427-432, 2008.

* cited by examiner

*Primary Examiner* — Tatyana Zalukaeva
*Assistant Examiner* — Ilya Treyger
(74) *Attorney, Agent, or Firm* — Lynn E. Barber

(57) ABSTRACT

A method is described for using a postoperative CSF dynamical examination to determine the CSF dynamical state of the patient and the dynamical state of the CSF shunt in conjunction therewith.

1 Claim, 2 Drawing Sheets

OPTIMIZATION OF HYDROCEPHALUS SHUNT SETTINGS

CROSS-REFERENCE TO RELATED APPLICATIONS

This application claims priority from U.S. Provisional Application Ser. No. 61/211,546 filed Mar. 31, 2009.

BACKGROUND OF THE INVENTION

1. Field of the Invention

The present invention relates to the use of an improved method of optimization of the settings and post-operative function of shunts used in hydrocephalus patients. Current methods and devices regarding shunting do not allow for real-time adjustment of cerebrospinal opening pressure of the specific patient in vivo. Shunts usually come in standard settings that can be adjusted after clinical assessment of the patient. The current invention allows for a real-time method to adjust shunt settings according to pressure and flow parameters of the specific patient in vivo, for initial shunt surgery, or for a shunt revision. Using this new method, the patient will be optimized in terms of real-time shunt settings, according to the patient's measured cerebrospinal pressure and flow information.

2. Description of the Related Art

Hydrocephalus is a condition affecting people who are unable to properly regulate their cerebrospinal fluid circulation. Cerebrospinal fluid (CSF) produced by the ventricular system is normally absorbed by the venous system. In a person suffering from hydrocephalus, the cerebrospinal fluid is not absorbed in this manner, but instead accumulates in the ventricles (free spaces) of the patient's brain. Normal pressure hydrocephalus (NPH) refers to a condition of pathologically enlarged ventricular size with normal pressures on lumbar puncture. If left untreated, an increasing volume of fluid can elevate the patient's intracranial pressure and can lead to serious medical conditions such as compression of the brain tissue and impaired blood flow to the brain.

The earliest description of hydrocephalus has been ascribed to Hippocrates (466-377 BC), who pointed out symptoms such as headache, vomiting and visual disturbance. Claudius Galen of Pergamon (130-200 AD) and medieval Arabian physicians also described hydrocephalus, believed to be due to an extracerebral accumulation of water.

Surgery to reduce fluid accumulation in the cerebrospinal fluid system was first performed by Le Cat in 1744, but it was not until the late nineteenth century, when sufficient pathophysiological knowledge and aseptic conditions were gained, that surgical procedures were truly introduced to treat hydrocephalus. In the 1960s, silicone and the invention of artificial valves led to a therapeutic breakthrough. With the development of an implantable shunt system to divert excess fluid, hydrocephalus went from being a fatal disease to becoming curable (Aschoff A, et al. Neurosurg Rev 22:67-93; discussion 94-5, 1999).

In 1965, Hakim and Adams described the newly discovered category of patients who also benefited from shunt surgery and who had normal cerebrospinal fluid pressure and benefited from shunt surgery (Hakim S and Adams R D. J Neurol Sci 2:307-27, 1965). The syndrome was named normal pressure hydrocephalus (NPH), and since then extensive work has been put into finding and developing new methods to identify those patients with NPH that will improve from shunt implantation surgery. Today, ventricular shunting is one of the most commonly performed neurosurgical procedures, including communicating and non-communicating hydrocephalus as well as shunt malformation. The annual incidence of operations varied between regional clinics from 2.3 to 6.3 per 100,000 inhabitants (Tisell M, et al. Acta Neurol Scand. 2005 August; 112(2):72-5.)

Shunting has dramatically changed the prognosis of people with hydrocephalus, many of them benefitting from normal life expectancies and regaining their baseline intelligence. The use of shunts, however, has created many unique problems of shunt dependence with frequent shunt revisions being the rule for most hydrocephalic patients. Shunt complications assume a major amount of all neurosurgeons' efforts.

CSF shunt implantation surgery involves establishing an accessory pathway for the flow of CSF in order to bypass an obstruction of the natural pathways. The shunt is positioned to enable the CSF to be drained from the cerebral ventricles or subarachnoid spaces into another absorption site, such as the right atrium of the heart or the peritoneal cavity, via a system of small tubes known as catheters. A regulatory device (known as a valve) can be inserted into the pathway of the catheters in order to regulate flow of CSF, depending on the pressure. This drainage enables the excess CSF within the brain to be evacuated and thereby, the pressure within the cranium to be reduced.

Valve mechanisms that continuously drain CSF are well known, as are valve mechanisms that control and/or adjust the opening pressure and/or drainage rate of the patient's CSF. However, currently available studies on determining what the optimal opening pressure of a hydrocephalus shunt should be are inconclusive. Earlier versions of the CSF shunt were fixed pressure shunts. The opening pressure of these shunts is fixed by the manufacturer, with three levels to choose from; a low pressure, medium pressure or high pressure valve. An example of such valves is the Hakim standard valves.

Today, in some hospitals the standard procedure is to start with a high opening pressure valve, and then adjust towards lower pressures if further improvement can be expected. In other hospitals the procedure is reversed. Thus the initial opening pressure chosen is low, and then increased if the patient experiences problems such as dizziness or other signs of over-drainage over time. The question of which shunt setting to start with was examined in a prospective Dutch study in 1998, comparing low versus high pressure shunt outcomes in 96 patients. Most differences in outcome between these two groups were statistically insignificant, even though the authors advised that patients with normal pressure hydrocephalus be treated with a low pressure shunt, (Boon A J et al. J. Neurosurg. 1998 March, 88(3):490-5).

When the adjustable shunt valve was introduced, such as the adjustable Codham Hakim programmable (CHP) valves, the possibility emerged of non-invasively adjusting and tailoring the opening valve pressure. A retrospective comparison of programmable shunt valves (CHP) vs. standard Hakim valves (H) was analyzed in 407 patients, to clarify whether CHP valves were advantageous compared to H valves, (Ringel F et al. Surg Neurol. 2005 January, 63(1):36-41.). Comparison was made with respect to valve-related shunt complications and surgical shunt revisions. The advantage implied with the Codham Hakim programmable valves did not translate into clinically significant findings, though the incidence of nontraumatic subdual hematomas and hygromas was higher in the CHP group. The authors therefore suggest it is still justified to implant standard Hakim valves in adult patients with hydrocephalus.

The studies mentioned above, on both fixed and adjustable valves, show that there is a need to be able to customize the opening pressure of a valve to the clinical needs of a patient who requires hydrocephalus surgery. One of the major issues in choosing valves is that there is no way of knowing what the actual opening pressure of a shunt will be once it is inserted into a patient. This is why the purpose of our invention herein is to use a postoperative CSF dynamical examination to determine the CSF dynamical state of the patient and CSF shunt in conjunction. Even if the in vitro settings of two shunts are the same, the resulting in vivo opening pressures will vary and depend on fluctuating individual conditions of the patients, such as differing abdominal pressure and compliance. By specific measurements and analyses, the actual resulting shunt opening pressure in vivo can be determined, and then adjusted according to a specific protocol to optimize shunt function. This can be accomplished by using our previously patented device for determining the hydrodynamics of the cerebrospinal fluid system, (WO 2006/091164).

The idea of the invention (WO 2006/091164) is to use the machine, which systematically generates or provides pressure and flow information, for determining with an uncertainty estimate, the hydrodynamic parameters of a patient in order to confirm diagnosis of hydrocephalus. The protocol can be based on a number of pressure-flow levels which are created by constant flow rates, flow rates that are varied according to a specific pattern, which generates a pressure fluctuation pattern, or adjustment of the flow while maintaining predetermined pressure levels. The machine can use predetermined time intervals for each pressure-flow level and automatically proceed to the next level when sufficient accumulated time with accepted data has been collected.

It is also possible to use signal analytic real-time methods, such as confidence intervals of a distribution, in order to estimate the accuracy or precision in the pressure and flow determined under each level and use this information to adaptively control when the examination shall proceed to the next pressure-flow level. Infusion is applied with cyclic variation in flow rate according to a predetermined pattern, superposed on one or more basic flow levels, and so, the response of pressure data is analyzed starting from or on the basis of a hydrodynamic model, with e.g. adaptive model-characterizing methods, such that values and the accuracy in estimated values for the patient's outflow resistance, resting pressure and compliance are continuously updated, whereupon the method is automatically proceeding to the next basic flow level when sufficient accuracy or precision has been obtained on one level.

Therefore, according to the invention herein, the dynamic information regarding the CSF pressure of the patient can also be gathered and interpreted as close to the patient's baseline, or resting pressure, when using the system described in (WO 2006/091164) or a similar system for measuring dynamic CSF pressure. The advantage this offers is that such dynamic information can, according to the invention herein, serve as a new method for real-time setting of the shunt pressure, as opposed to getting a static clinical picture of the patient and implanting a shunt that may not be optimal, even if it is adjustable. This would provide higher quality care to the patient, and reduce the cost of related healthcare.

A related patent, JP11299742A, can offer similar information regarding CSF pressure compared to WO 2006/091164. However, unlike the invention herein, this patent is based on resistance values against CSF absorption rather than continuous pressure measurements, and offers no method of dynamically measuring in vivo shunt opening pressure values. The method is manual and has no security connections between pump and pressure measurement and is therefore regarded as technically difficult to carry through as well as for final analysis. Drawbacks are that the precision of a determination based on two points as well as determination of a dynamic parameter in such a short time as 5 to 10 minutes is low and no statistic uncertainties are recorded.

Another method to set programmable shunts is described by Miyake et al (Neurol Med Chir (Tokyo) 48, 427-432, 2008). They use the patient's height and body-mass index to estimate the hydrostatic pressure and intraabdominal pressure giving an initial shunt setting. Another common technique used to clinically assess and guide shunt settings is the lumbar tap test. This is a relatively common test that can be done as an office procedure. Using lumbar puncture, 30 to 50 ml of CSF is removed with documentation of the patient's gait and cognitive function before and 30 to 60 minutes after the procedure. This is sometimes called the Fisher test. Common parameters measured before and after CSF removal includes measures of gait speed, stride length, reaction time, and tests of verbal memory and visual attention.

However, unlike the invention herein, those techniques do not measure resting CSF pressure, and do not allow for in vivo resulting shunt opening pressure to be determined.

SUMMARY OF THE INVENTION

It is an object of the invention to provide an improved and more accurate method for optimizing the CSF opening pressure setting of an implantable shunt, for initial shunt placement or shunt surgery revision. When performing a postoperative CSF dynamical examination with supplemental analyses, the true function of the shunt in the environment where it is intended to work can now be determined. Normally, the parameters of the shunt are only determined in standard bench tests, but this cannot account for differences inferred by individual patients and their natural pressure fluctuations. By assessing the in vivo function of the shunt, the optimal opening pressure can be determined and thereby guide the setting of an implantable shunt. During a postoperative CSF dynamical examination, the intracranial pressure is regulated to several different levels, and the flow needed to maintain these levels is calculated. This results in a pressure/flow diagram, and the slope of the curve corresponds to the combined outflow conductance of the patient and the CSF shunt. The point of intercession of the regression line and the x-axis corresponds to the opening pressure of the shunt.

Other objects and advantages will become obvious to the reader and it is intended that these objects and advantages are within the scope of the present invention.

To illustrate how the results from a postoperative CSF dynamical examination can be used for optimization of shunt opening pressure, two diagrams from different postoperative examinations are included in the figures herein.

DETAILED DESCRIPTION OF THE INVENTION
AND PREFERRED EMBODIMENTS THEREOF

Figure 3:
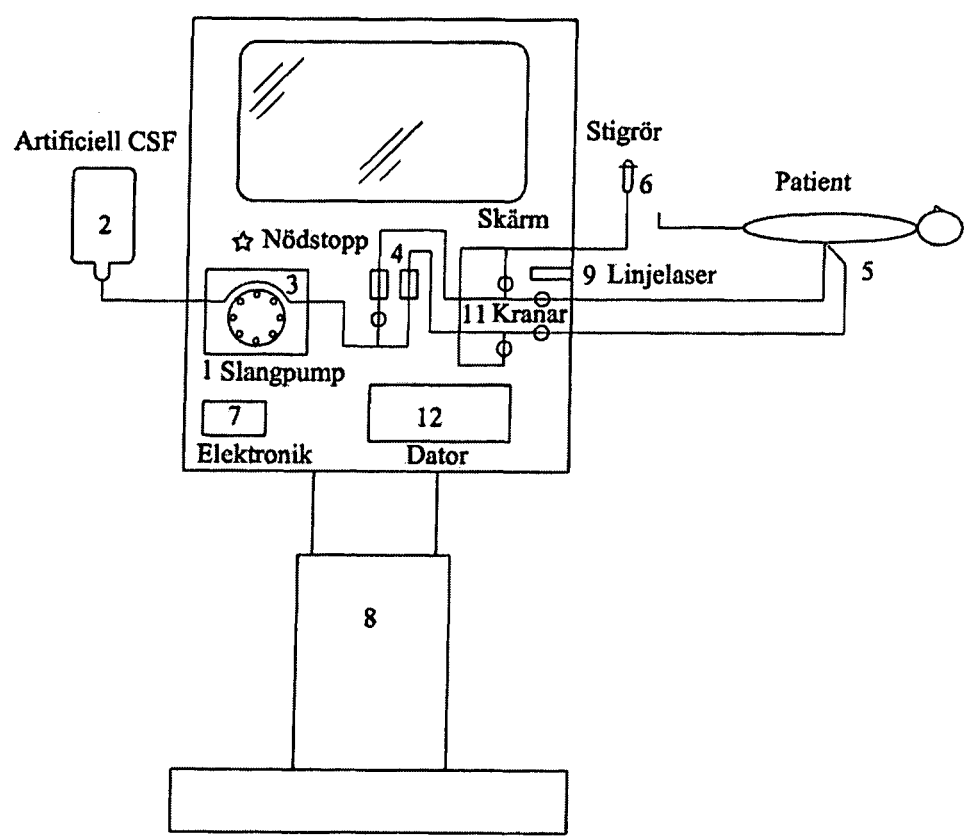
FIG. 3 is a schematic drawing of an instrument, for example a model named CELDA™, that may be used to perform the method of the invention herein.

The invention herein describes a new method to use a postoperative CSF dynamical examination to determine the CSF dynamical state of the patient and the dynamical state of the CSF shunt in conjunction. The dynamical state of the CSF can be determined using the instrument provided in the disclosure of patent WO 2006/091164, the disclosure of which is incorporated herein by reference (FIG. 3). A new method can be applied during the placement or readjustment of various shunts on the market in order to optimize shunt choice and setting, which is safer for the patient and with improved indication of disturbances in a patient with hydrocephalus.

The device, for example a CELDA™ instrument, for carrying through the method according to the invention for measuring the hydrodynamic properties of the CSF system, is shown in FIG. 3. The device comprises a peristaltic pump 1 for infusion of artificial CSF from a container 2, e.g. a bottle or bag therefor. The artificial CSF is fed by the pump 1 from the container 2 through pump tubing 3 and pressure transducers 4 for continuous registration of the intracranial pressure to a contact object 5 for defining or establishing lumbarly, through the spinal canal, double fluid contacts with the CSF system. The contact object 5 consists of two needles or of one needle or catheter with double lumen. Artificial CSF or a similar fluid as known in the art is pumped by means of the pump 1 through one passage into or out of the CSF system. By means of the standardized pressure transducers 4 the pressure is measured through both passages.

In the embodiment having two needles, needles are preferably used which according to the invention have a number of additional holes drilled on the sides at the point of the needles. In this way, a better contact with the CSF system is obtained obstruction of the pump needles is avoided when soft tissue in the spinal canal is drawn towards the needle when pumping fluid out of the system.

The advantage with the alternative embodiment with the new double lumen needle and double lumen catheter is that the device only need have one input passage. Regarding the solution with the double lumen catheter, the investigation or examination can be carried out even in a normal hospital bed. Needles require a special bed with a hole in the back through which the needles can be inserted into the spinal canal.

The catheter solution and the pressure measuring function of the equipment also renders it possible, after the infusion test is finished and without any new surgical operation, to carry out other predictive tests for hydrocephalus investigation, e.g. a long-term measurement or a so called tap test, described above.

The device for use according to the invention preferably further comprises a computer 12 with software for computerized collection and analysis as well as control of the pump speed. A calculation unit, forming part of the software of the computer, is controlled by the software to use the adaptive method which at each pressure-flow level considers the time of measure and the patient's fluctuations in physiologic signals for calculating, in real time, when the relation between measured time and measured accuracy in pressure and flow on the actual level is sufficient. When the relation between measured time and measured accuracy on the actual level is sufficient, the software is designed and constitutes means for initiating the next pressure-flow level according to a predetermined protocol, for example using a CELDA™ instrument and software (FIG. 3) (Likvor A B, Tvistevägen 47, 907 19, Umea, Sweden). Furthermore, the software is designed for real-time analysis, i.e. constitutes means for real-time analysis for, from the pressure-flow information from the examination, determining and giving an account of the patient's hydro-dynamic parameters with an uncertainty estimate.

The calculation unit can also be designed to estimate the accuracy in the determined pressure and flow on each pressure-flow level in real time by means of signal analytic methods as defined above, and by means of this information adaptively control when to proceed to the next level, or to carry through a measurement during a predetermined time interval at each pressure-flow level.

Pump 1 is controlled to apply infusion with cyclic variation in flow velocity according to a given pattern, superposed on one or more basic flow levels, and the calculation unit is further designed to analyze the response of pressure data emanating from the hydrodynamic model such that values and the accuracy of estimated values for the patient's outflow resistance, resting pressure and compliance are continuously updated, whereupon the software automatically initiates the next basic flow level when sufficient accuracy on one level has been reached.

The software is further designed to directly eliminate, as defined above, measured intervals with signal variations depending on known circumstances, errors noted by a built-in safety system or incidents registered by the operator. The software is also designed to calculate and present a final statistic estimate of the resulting precision in the determined parameters.

The advanced and time consuming calibration routines of the prior system are avoided by using a standardized tube set with the pump tube 3, the statistic variation of which from tube set to tube set is carefully tested. Furthermore, a simple combined calibration test of pressure transducers 4 as well as pump system 1, 3 is carried out prior to each examination. The apparatus for the calibration test consists of a vertically located stand pipe 6, integrated in the tube system, which is automatically filled by the pump 1 to a predetermined volume. The pressure increase due to the increased height of the column is registered by the pressure transducers 4 and automatically controlled in view of given deviation standards. In this manner, the accuracy in flow measurement as well as pressure measurement is tested in an automated procedure.

The type of invasive investigation or examination as provided in the procedure herein makes great demands upon assessing the safety of the patient. An active infusion is used for regulating or controlling the intracranial pressure, but if the pressure gets too high or too low, the patient is put in a life-threatening condition. Existing infusion equipment for this type of measurements contains no built-in safety routines, but leaves the entire responsibility to the operator. The present invention includes a plurality of new technical solutions for eliminating generation of injurious pressures due to defects in the hardware and software of the equipment.

One potential danger of all automated techniques except the invention is if the software does not operate properly and generates a control signal which is not related to the actual pressure. This is solved in the invention by means of a toggle signal between the electronics/hardware 7 and the computer/software 12 of the device controlling that the software operates properly. If the toggle signal is not sent continuously, the pump 1 is stopped by the hardware 7.

Control to insure that the intracranial pressure is within the allowed range is made internally by the electronics/hardware 7, which otherwise stops the pump 1 and sends an error message to the computer/software 12. Control to insure that the intracranial pressure is within the allowed range is alternatively made by the software, whereby the pump 1 is brought to a stop at injurious pressures and an error message is presented. Control to insure that the pressure measurement is intact is made by comparing the pressure from the two fluid passages and by controlling that there are pulsations related to the cardiac cycle in the pressure signal. By deviations the pump 1 is stopped.

When measuring a physiologic pressure through fluid tubes, it is important to compensate for static errors generated because of hydrostatic columns in the tubes. This compensation can be done in the invention by locating and clearing the pressure transducers 4 at the zero level of the patient (for the intracranial pressure this means at the ear canal). In order to facilitate this level location, the entire apparatus, including the transducers 4, is mounted on an electrically elevated pillar 8. The equipment also includes a horizontally suspended linear laser 9 which generates a horizontal line on a level with the level of the transducers. In this way, the operator can easily compensate for any hydrostatic parts by guiding the pillar 8 such that the line is located at the ear canal of the patient.

In one embodiment a sterilized standardized tube set is used, which includes a pump tube 3 which is adapted to the peristaltic pump 1, two disposable pressure transducers 4, stopcocks 11 and tubes from the CSF container 2 to the patient. Everything is mounted on a plastic sheet for easy mounting on the pillar 9.

By performing a CSF dynamical examination utilizing several different pressure levels or infusion flow velocities, the opening pressure of the shunt in vivo can be determined as the intersection of the pressure/flow-curve and the pressure axis. The in vivo opening pressure of the shunt is composed of the in vitro shunt opening pressure in addition to the patient abdominal pressure, compliance and physiological fluctuations. The abdominal pressure, compliance and physiological fluctuations may be combined into a quantity which here is called $P_{resistive}$, and it can vary significantly between patients. Thus, the in vivo opening pressure of each individual patient may not be predicted beforehand but must be measured.

The driving pressure through the CSF shunt is the differential pressure between the intracranial pressure (ICP), $P_{resistive}$ and the shunt opening pressure in vitro ($P_{open}$). That is $$P_{drive} = ICP - P_{resistive} - P_{open}$$

and so $$\text{Flow through shunt} = P_{drive}/R_{shunt}$$

where $R_{shunt}$ is the resistance of the CSF shunt. CSF will flow through the shunt if and only if $P_{drive}$ is larger than the shunt opening pressure in vivo. Thus, the most optimal situation for the patient is if the shunt is open at the optimal resting pressure of the patient, $P_{rest}$, and above, but not below. To reassure that this is the case, the shunt opening pressure should be adjusted the amount of steps necessary to compensate for the pressure difference found between the shunt opening pressure in vivo and $P_{rest}$ during the CSF dynamical examination, which is the same as setting the in vitro shunt opening pressure equal to $P_{drive}$. This problem is solved with this unique invention since the needed adjustment is deduced from the examination, using for example a CELDA™ instrument and the shunt can be adjusted accordingly.

Figure 1:
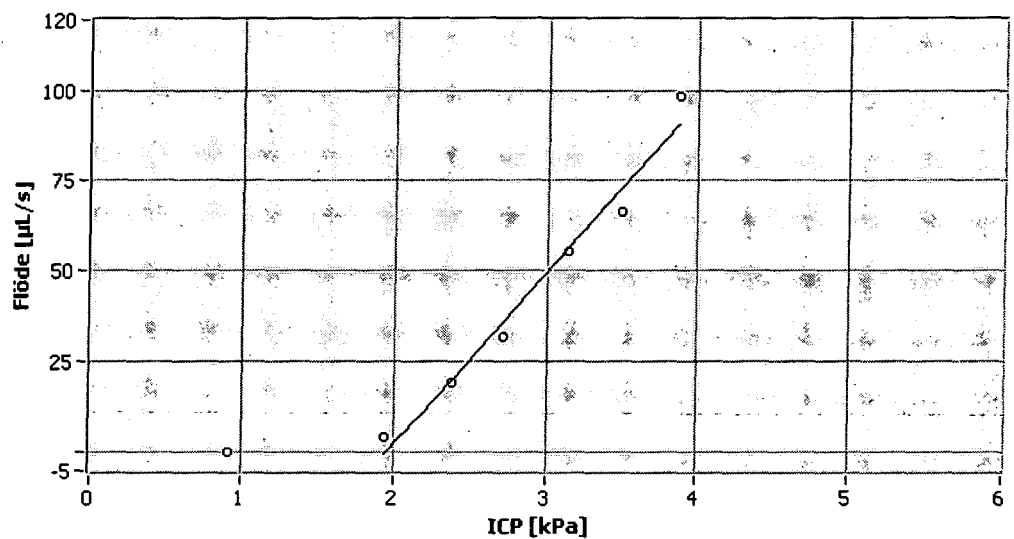
FIG. 1 is a graph of Flow (micro liter) vs. ICP-Inter Cranial Pressure (kPa) This patient has a resting pressure of 0.9 kPa, but the opening pressure of the shunt is 2.0 kPa, thus the shunt is not open in the normal everyday living of the patient. The opening pressure of the shunt needs to be adjusted as to be equal to the resting pressure of the patient in order to optimize efficacy.
Figure 2:
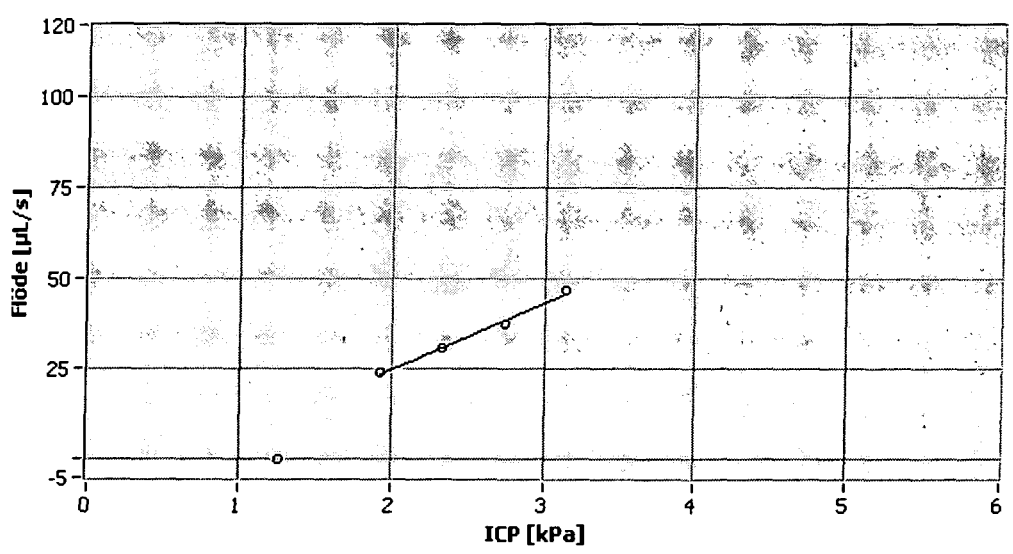
FIG. 2 is a graph of Flow (micro liter) vs. ICP-Inter Cranial Pressure (kPa). This patient has a resting pressure of 1.3 kPa, but the opening pressure of the shunt is 0.7 kPa. Thus the shunt is likely to produce an excessive flow of CSF in the everyday living of the patient, with adherent symptoms of over drainage for the patient. The opening pressure of the shunt needs to be adjusted as to be equal to the resting pressure of the patient in order to optimize efficacy.

Two different situations are represented in FIGS. 1 and 2. In FIG. 1, the patient has a resting pressure that is lower than the opening pressure of the shunt while in the second case, represented in FIG. 2 the patient's resting pressure is higher than the shunt's opening pressure. In both cases the shunt needs to be adjusted in order to optimize the efficacy of the system.

The purpose of the following examples is not limited to, but can be used to, see how the method of the invention can be done with different types and manufacture of shunts with for example a CELDA™ instrument.

EXAMPLE 1

Use of CODMAN® HAKIM® Programmable Valve System

The CODMAN® HAKIM® Programmable Valve System (Codman Inc., 325 Paramount Drive, Raynham, Mass. 0276, USA) enables surgeons to pre-select one of 18 different pressure settings between 30 mm and 200 mm H2O. Given the adjustable nature of this shunt, it may be used in conjunction and in vivo with the invented method of optimizing shunt settings herein. Surgeons change the opening pressure of the valve through the use of an externally applied, codified magnetic field. The valve contains a ball and spring mechanism that sits atop a rotating spiral cam that contains a stepper motor. When the surgeon applies a specific magnetic field to the stepper motor, the cam turns slightly, increasing or decreasing the tension in the spring and ball, which changes the opening pressure of the valve.

For a patient, the in vitro shunt opening pressure was set to 1.5 kPa (kilopascal), and it was determined during the postoperative CSF dynamical examination using a CELDA™ instrument (Likvor A B, Tvistevägen 47, 907 19, Umea, Sweden) that the resting pressure of the patient was 1.5 kPa and the in vivo shunt opening pressure was 1.9 kPa. This indicates that the abdominal pressure, compliance and other influencing factors constitute a resistive pressure ($P_{resistive}$) corresponding to 0.4 kPa. Hence, as a result of the CSF dynamical examination, if the resting pressure was the same as the optimal resting pressure, the shunt opening pressure would be tuned down 0.4 kPa to ensure that the shunt was functioning correctly, and not "under shunting", in the everyday living of the patient. For a patient with an optimal resting pressure x kPa lower than the measured resting pressure, the shunt would have been turned down 0.4+x kPa.

The resistive pressure cannot be explicitly measured since it is dependent on several different physiological parameters, and thus the only way to implicitly determine the inter-patient influence on the shunt opening pressure, is by using a CSF dynamical examination.

EXAMPLE 2

Use of SOPHY® Adjustable Pressure Valves

Sophysa USA, Inc. (303 S Main Street, Crown Point, Ind. 46307, USA) was a pioneer in adjustable valves by launching the first adjustable pressure valve in 1985. More than 55,000 SOPHY® Adjustable Pressure Valves were implanted in patients throughout the world between 1985 and 2003. SOPHY® Adjustable Pressure Valves provide a range of 8 pressure settings, from 30 mm to 200 mm H2O. The SOPHY® Adjustable Pressure Valve also uses a ball and spring design. The spring is attached to a magnetic rotor whose position can be non-invasively altered using an adjustment magnet. Given the adjustable nature of this shunt, it may be used in conjunction and in vivo with the invented method of optimizing shunt settings herein.

For a patient the in vitro shunt opening pressure was set to 1 kPa, and it was determined during the postoperative CSF dynamical examination that the resting pressure of the patient was 2 kPa and the in vivo shunt opening pressure was 1.3 kPa. This indicates that the abdominal pressure, compliance and other influencing factors constitute a resistive pressure ($P_{resistive}$) corresponding to 0.3 kPa. Hence, as a result of the CSF dynamical examination, if the resting pressure was the same as the optimal resting pressure, the shunt opening pressure would be tuned up 0.7 kPa to ensure that the shunt was functioning correctly, and not over shunting, in the everyday living of the patient. For a patient with an optimal resting pressure x kPa higher than the measured resting pressure, the shunt would have been tuned up 0.7+x kPa.

EXAMPLE 3

Use of ®

The PS Medical Strata valve (Medtronic Inc., 710 Medtronic Pkwy, Minneapolis, Minn. 55432, USA) is an adjustable flow control valve in which the resistance properties of the valve can be changed non-invasively by the caregiver. It is designed to minimize overdrainage of cerebrospinal fluid (CSF) and maintain intraventricular pressure (IVP) within a normal physiologic range, regardless of patient position. The normally closed Delta chamber mechanism opens in response to positive ventricular pressure. Working with the ball and spring valve, this mechanism minimizes overdrainage by utilizing the principle of hydrodynamic leverage. Given the adjustable nature of this shunt, it may be used in conjunction and in vivo with the invented method of optimizing shunt settings herein.

For one patient, the in vitro shunt opening pressure was set to 2 kPa, and it was determined during the postoperative CSF dynamical examination, using the CELDA™ instrument, that the resting pressure of the patient was 1.5 kPa and the in vivo shunt opening pressure was 2.1 kPa. This indicates that the abdominal pressure, compliance and other influencing factors constitute a resistive pressure ($P_{resistive}$) corresponding to 0.1 kPa. Hence, as a result of the CSF dynamical examination, if the resting pressure was the same as the optimal resting pressure, the shunt opening pressure would be tuned down 0.6 kPa to ensure that the shunt was functioning correctly, and not under shunting, in the everyday living of the patient. For a patient with an optimal resting pressure x kPa higher than the measured resting pressure, the shunt would have been turned down 0.6−x kPa.

EXAMPLE 4

Use of PROGAV®

The PROGAV® is a position-dependent valve (Miethke GMBH, Ulanenweg 2, D-14469 Potsdam, Germany) The opening pressure of the valve varies continuously with the patient's body position. To adapt the PROGAV® to the individual patient, one opening pressure is selected for the supine position and one for the upright position. The opening pressure for the supine position is defined exclusively by the adjustable valve. The gravitational unit does not influence the opening pressure in this body position. The opening pressure can be set to a value between 0 and 20 cm H2O, depending on clinical presentation and indication. Given the adjustable nature of this shunt, it may be used in conjunction and in vivo with the invented method of optimizing shunt settings herein.

For one patient the in vitro shunt opening pressure was set to 0.4 kPa, and it was determined during the postoperative CSF dynamical examination, using the CELDA™ instrument, that the resting pressure of the patient was 0.9 kPa and the in vivo shunt opening pressure was 0.6 kPa. This indicates that the abdominal pressure, compliance and other influencing factors constitute a resistive pressure (Presistive) corresponding to 0.4 kPa. Hence, as a result of the CSF dynamical examination, if the resting pressure was the same as the optimal resting pressure, the shunt opening pressure would be tuned up 0.3 kPa to ensure that the shunt was functioning correctly, and not over shunting, in the everyday living of the patient. For a patient with an optimal resting pressure x kPa lower than the measured resting pressure, the shunt would have been tuned up 0.3−x kPa.

EXAMPLE 5

Clinical Study Resting Pressure

A study is performed to determine if the shunt opening pressure in vivo is the same as the resting pressure. The study contains 20 patients. In the postoperative CSF dynamical examination, the resting pressure of the patient is determined. After finishing the study, all shunts are adjusted according to recommended medical procedures.

The hypothesis of the study is that if the shunt opening pressure in vivo, is the same as the resting pressure of the patient, the relationship between maximum clinical improvement and minimum side effects will be optimized.

The patients have previously been treated by shunt surgery according to the selection criteria being used today. These patients have prior to surgery been examined by a CSF dynamical examination, as well as a clinical evaluation. Approximately three months after surgery patient improvement is registered, and another CSF dynamical examination is performed to ensure that the CSF shunt is working properly.

In the postoperative CSF dynamical examination, the resting pressure of the patient is determined. By increasing the intracranial pressure of the patient to several different levels, the outflow conductance of the patient in conjunction with the shunt is determined as the slope of the resulting pressure and flow curve. It can also be calculated from this pressure-flow curve, at what pressure the shunt initially opens, a pressure referred to as the opening pressure of the shunt. Thus, half of the study population, randomly selected, will be subjected to adjustments of the shunt opening pressure following the results of their postoperative CSF dynamical examination. The other half will not have their shunts adjusted.

A second estimation of improvement will then be performed for the entire group, and from this it can be evaluated whether the improvement in the adjusted group was significantly larger than the improvement in the non-adjusted group. After finishing the study all shunts may be adjusted in the way recommended by the physician.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method of optimizing hydrocephalus shunt settings, providing a device comprising:

a peristaltic pump for infusion of artificial cerebrospinal fluid from a container through pump tubing, and pressure transducers for continuous registration of the intracranial pressure to a contact object with two passages for defining or establishing lumbarly, through the spinal canal, double fluid contacts with the cerebrospinal fluid system;

the method comprising a real-time adjustment of cerebrospinal pressure of a specific patient in vivo, wherein the real-time adjustment is done according to pressure and flow parameters of the specific patient in vivo, for initial shunt surgery, or for post-operative shunt revision, wherein the shunt opening pressure is adjusted to compensate for the pressure difference found between the shunt opening pressure in vivo and the patient abdominal pressure, compliance and physiological fluctuations during the cerebrospinal fluid dynamical examination.

* * * * *